United States Patent
Gonzalez et al.

(10) Patent No.: US 12,429,475 B2
(45) Date of Patent: Sep. 30, 2025

(54) METHODS AND SYSTEMS FOR CAPTURING BIOLOGICAL SAMPLES FROM A HEPA FILTER ON AN AIRCRAFT

(71) Applicant: B/E AEROSPACE, INC., Winston Salem, NC (US)

(72) Inventors: Arnau Castillo Gonzalez, Maarssen (NL); Brian St. Rock, Andover, CT (US); Antonio Martinez Murcia, Elche (ES)

(73) Assignee: B/E AEROSPACE, INC., Winston-Salem, NC (US)

( * ) Notice: Subject to any disclaimer, the term of this patent is extended or adjusted under 35 U.S.C. 154(b) by 953 days.

(21) Appl. No.: 17/518,332

(22) Filed: Nov. 3, 2021

(65) Prior Publication Data

US 2022/0155191 A1    May 19, 2022

Related U.S. Application Data

(60) Provisional application No. 63/114,400, filed on Nov. 16, 2020, provisional application No. 63/114,330, filed on Nov. 16, 2020, provisional application No. 63/114,350, filed on Nov. 16, 2020, provisional application No. 63/114,157, filed on Nov. 16, 2020, provisional application No. 63/114,366, filed on Nov. 16, 2020, provisional application No. 63/114,386, filed on Nov. 16, 2020, provisional application No. 63/114,064, filed on Nov. 16, 2020, provisional application No. 63/114,339, filed on Nov. 16, 2020.

(51) Int. Cl.

| | |
|---|---|
| *G01N 33/497* | (2006.01) |
| *B01L 1/00* | (2006.01) |
| *B01L 3/00* | (2006.01) |
| *B01L 3/02* | (2006.01) |
| *B01L 7/00* | (2006.01) |
| *B64D 13/08* | (2006.01) |
| *C12Q 1/04* | (2006.01) |
| *C12Q 1/686* | (2018.01) |
| *C12Q 1/70* | (2006.01) |
| *G01N 1/10* | (2006.01) |
| *G01N 1/22* | (2006.01) |
| *G01N 1/40* | (2006.01) |
| *G16B 10/00* | (2019.01) |
| *G16B 40/00* | (2019.01) |
| *G16B 50/10* | (2019.01) |
| *B64D 13/06* | (2006.01) |
| *H04L 67/12* | (2022.01) |

(52) U.S. Cl.
CPC .............. *G01N 33/497* (2013.01); *B01L 1/00* (2013.01); *B01L 3/021* (2013.01); *B01L 3/505* (2013.01); *B01L 7/52* (2013.01); *B64D 13/08* (2013.01); *C12Q 1/04* (2013.01); *C12Q 1/686* (2013.01); *C12Q 1/70* (2013.01); *G01N 1/10* (2013.01); *G01N 1/2226* (2013.01); *G01N 1/2247* (2013.01); *G01N 1/40* (2013.01); *G16B 10/00* (2019.02); *G16B 40/00* (2019.02); *G16B 50/10* (2019.02); *B01L 2200/028* (2013.01); *B01L 2200/10* (2013.01); *B01L 2200/18* (2013.01); *B01L 2300/023* (2013.01); *B01L 2300/18* (2013.01); *B64D 13/06* (2013.01); *B64D 2013/0603* (2013.01); *G01N 2001/1031* (2013.01); *G01N 1/2205* (2013.01); *G01N 2001/2244* (2013.01); *G01N 33/4975* (2024.05); *H04L 67/12* (2013.01)

(58) Field of Classification Search
CPC ...... G01N 33/497; G01N 1/10; G01N 1/2226; G01N 1/2247; G01N 1/40; G01N 1/2205; G01N 33/4975; G01N 2001/1031; G01N 2001/2244; G01N 2001/2217; G01N 1/2211; G01N 1/2214; B01L 1/00; B01L 3/021; B01L 3/505; B01L 7/52; B01L 2200/028; B01L 2200/10; B01L 2200/18; B01L 2300/023; B01L 2300/18; B64D 13/08; B64D 13/06; B64D 2013/0603; B64D 11/00; C12Q 1/04; C12Q 1/686; C12Q 1/70; G16B 10/00; G16B 40/00; G16B 50/10; H04L 67/12

See application file for complete search history.

(56) References Cited

U.S. PATENT DOCUMENTS

| | | |
|---|---|---|
| 6,491,254 B1 | 12/2002 | Walkinshaw et al. |
| 2004/0208804 A1 | 10/2004 | Hall et al. |
| 2009/0035770 A1 | 2/2009 | Mathies et al. |
| 2012/0122075 A1 | 5/2012 | Call et al. |

(Continued)

FOREIGN PATENT DOCUMENTS

| | | | | |
|---|---|---|---|---|
| WO | WO-2005069753 A2 | * | 8/2005 | .............. A61L 2/087 |
| WO | WO-2006138375 A2 | * | 12/2006 | ........... G01N 1/2205 |

OTHER PUBLICATIONS

Cox et al Comparison of indoor air sampling and dust collection methods for fungal exposure assessment using quantitative PCR, Environ.Sci.processes impacts, 2017,19, 1312 (Year: 2017).*

(Continued)

*Primary Examiner* — Narayan K Bhat
(74) *Attorney, Agent, or Firm* — SNELL & WILMER L.L.P.

(57) ABSTRACT

A method for collecting an aircraft cabin representative biological sample from an aircraft HEPA (high efficiency particulate air) filter including collecting a used HEPA filter after flight, transferring the HEPA filter to a remote location, processing the HEPA filter in order to remove an air sample, and concentrating the collected sample to be used on a pathogen identifying tester.

19 Claims, 3 Drawing Sheets

(56) References Cited

U.S. PATENT DOCUMENTS

2016/0025603 A1\* 1/2016 Kindt ............... G01N 33/56983
            422/534
2017/0009290 A1  1/2017 Ahmad et al.
2019/0046985 A1  2/2019 Kang et al.

OTHER PUBLICATIONS

Korves, T.M., et al., "Bacterial communities in commercial aircraft high-efficiency particulate air (HEPA) filters assessed by PhyloChip analysis:", Indoor Air, vol. 23, No. 1, Jun. 8, 2012 (Jun. 8, 2012), pp. 50-61, XP055907740, DK ISSN: 0905-6947, DOI: 10.1111/j.1600-0668.2012.00787.x.
Osman, S., et al., "Microbial burden and diversity of commercial airline cabin air during short and long durations of travel", The ISME Journal, vol. 2, No. 5, May 1, 2008 (May 1, 2008), pp. 482-497, XP055906178, London, ISSN: 1751-7362, DOI: 10.1038/ismej.2008.11. Retrieved from the Internet: URL :<https://www.nature.com/articles/ismej2> 00811.pdf>.
Extended European Search Report for European Patent Application No. EP21208606.0, dated Apr. 13, 2022.
European Patent Office, European Search Report dated Sep. 5, 2024 in Application No. 24169276.3.
Extended European Search Report for European Patent Application No. EP21208622.7, dated Apr. 14, 2022.
Korves T.M., et al, "Bacterial communities in commercial aircraft high-efficiency particulate air (HEPA) filters assessed by PhyloChip analysis"; Indoor Air, vol. 23, No. 1, Jun. 8, 2012 (Jun. 8, 2012), pp. 50-61, XP055907740, DK; ISSN: 0905-6947, DOI: 10.1111/j.1600-0668.2012.00787.x; sections "Practical Implications"; "Materials and methods", "Aircraft and outdoor air samples"; first and second paragraph; "PCR amplification of 16S rRNA genes".

\* cited by examiner

100

102
Collecting a used HEPA filter after flight

104
Transferring the HEPA filter to a remote location

106
Processing the HEPA filter in order to remove an air sample

108
Concentrating the collected sample to be used on a pathogen identifying test, such as a PCR tester

Fig. 1

METHODS AND SYSTEMS FOR CAPTURING BIOLOGICAL SAMPLES FROM A HEPA FILTER ON AN AIRCRAFT

PRIORITY CLAIM

This application claims priority to and the benefit of U.S. Provisional Patent Application 63/114,330 filed on Nov. 16, 2020, entitled "METHODS FOR BIOLOGICAL SAMPLE CAPTURE FROM A HEPA FILTER ON AN AIRCRAFT," and claims priority to and the benefit of U.S. Provisional Patent Application 63/114,339 filed on Nov. 16, 2020, entitled "METHODS TO OBTAIN A BIOLOGICAL SAMPLE REPRESENTATIVE OF A PASSENGER CABIN ON AN AIRCRAFT USING FILTER MATERIAL PIECES," and claims priority to and the benefit of U.S. Provisional Patent Application 63/114,350 filed on Nov. 16, 2020, entitled "METHODS TO OBTAIN A BIOLOGICAL SAMPLE REPRESENTATIVE OF A PASSENGER CABIN ON AN AIRCRAFT USING AN AIR CYCLONIC COLLECTOR," and claims priority to and the benefit of U.S. Provisional Patent Application 63/114,064 filed on Nov. 16, 2020, entitled "METHODS TO OBTAIN A BIOLOGICAL SAMPLE REPRESENTATIVE OF A PASSENGER CABIN OF AN AIRCRAFT THROUGH THE CABIN EXHAUST VALVE," and claims priority to and the benefit of U.S. Provisional Patent Application 63/114,366 filed on Nov. 16, 2020, entitled "GALLEY INSERT FOR AIRCRAFTS WITH CAPABILITIES TO PERFORM A PCR TEST," and claims priority to and the benefit of U.S. Provisional Patent Application 63/114,157 filed on Nov. 16, 2020, entitled "METHODS TO OBTAIN A BIOLOGICAL SAMPLE REPRESENTATIVE OF A PASSENGER CABIN ON AN AIRCRAFT AUTOMATICALLY FROM THE COLLECTOR DEVICE," and claims priority to and the benefit of U.S. Provisional Patent Application 63/114,386 filed on Nov. 16, 2020, entitled "METHODS TO PROCESS A BIOLOGICAL SAMPLE REPRESENTATIVE OF A PASSENGER CABIN ON AN AIRCRAFT," and claims priority to and the benefit of U.S. Provisional Patent Application 63/114,400 filed on Nov. 16, 2020, entitled "USE OF BIOLOGICAL SAMPLE REPRESENTATIVE OF A PASSENGER CABIN ON AN AIRCRAFT TO SEARCH FOR NON-DESCRIBED EMERGING PATHOGENS," all of which are herein incorporated by reference in their entirety for all purposes.

BACKGROUND

Technological Field

The present application is related to a system and method used to collect a representative air sample of an aircraft, more specifically to a method and systems for capturing biological samples from a HEPA filter on an aircraft.

Description of Related Art

The spread progression of SARS-CoV-2 around the world has brought attention to the systemic risks of economic globalization. As a result of the COVID-19 pandemic there is a need for better monitoring, detecting, and isolating ill passengers, specifically due to the detrimental impact on the global economy, to prevent the spread of COVID-19 and other pathogens during travel, e.g. air travel, rail travel or the like, due to closed borders, movement restrictions, and testing requirements.

The COVID-19 pandemic the air travel industry has proven that air travel can be safe and that aircraft cabins have a well-managed airflow that inhibits transmission of virus, and that being seated onboard an aircraft is safer than shopping in large stores. Governments and other authorities, however, need to assume that aircraft are contaminated until proven "clean", as 25% of COVID-19 cases are asymptomatic or pre-symptomatic; but still contagious. To date, travelers and governments have relied on individual tests. Testing for viruses requires that samples be taken of various bodily tissues and/or fluids. An adequate concentration of material is needed, the concentration being determined by the type and sensitivity of the testing procedure. It could be difficult to get adequate samples from travelers for the purposes of virus detection, contact tracing in the event of an exposure, etc. It is also possible that the airline is required to certify the arriving aircraft as being "virus free".

Accordingly, conventional systems and methods of monitoring infections has not lived up to requirements of the fast-paced modern world. Thus, there is still a need in the art for improved virus and pathogen detection system. The present disclosure provides a solution for this need.

SUMMARY OF THE INVENTION

A method for collecting a representative sample from an aircraft HEPA filter includes collecting a used HEPA filter after flight, transferring the HEPA filter to a remote location, processing the HEPA filter in order to remove an air sample, and concentrating the collected sample to be used on a pathogen identifying test, such as a Polymerase Chain Reaction (PCR) test. The HEPA filter can afterwards be washed and made available for aircraft retrofit. The HEPA filter is configured and adapted to clean air flowing through a recirculation flow path.

The samples can be removed by inverted flow or by using centrifugal wash. The centrifugal wash can employ a sterile buffer for washing. Processing can include removing the sample with a handheld tool with a sponge, such that the sponge can be dragged across the HEPA filter in order to collect the sample. The sponge can be processed through a sample concentration and purification process before undergoing a pathogen identifying test, such as a Polymerase Chain Reaction (PCR) test.

It is also considered that the method includes removing a portion of the HEPA filter. The portion can be a flexible brace and replacing the flexible brace with a new brace prior to the next flight.

A system for collecting a representative sample from an aircraft HEPA filter is also disclosed. The system includes a HEPA filter positioned in a recirculation flow path of an aircraft configured to collect flow path air, and at least one removable strip attached to the strip for removing after each flight. The removable strip can be flexible. The HEPA filter can be accessible from inside the aircraft. It is also considered that the system can include a handheld wand for scrubbing a portion of the HEPA filter and removing a sample, wherein the handheld wand includes a sponge on at least a first end thereof.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIG. 1 is a block diagram of a method of the disclosure;

DETAILED DESCRIPTION

Figure 2:
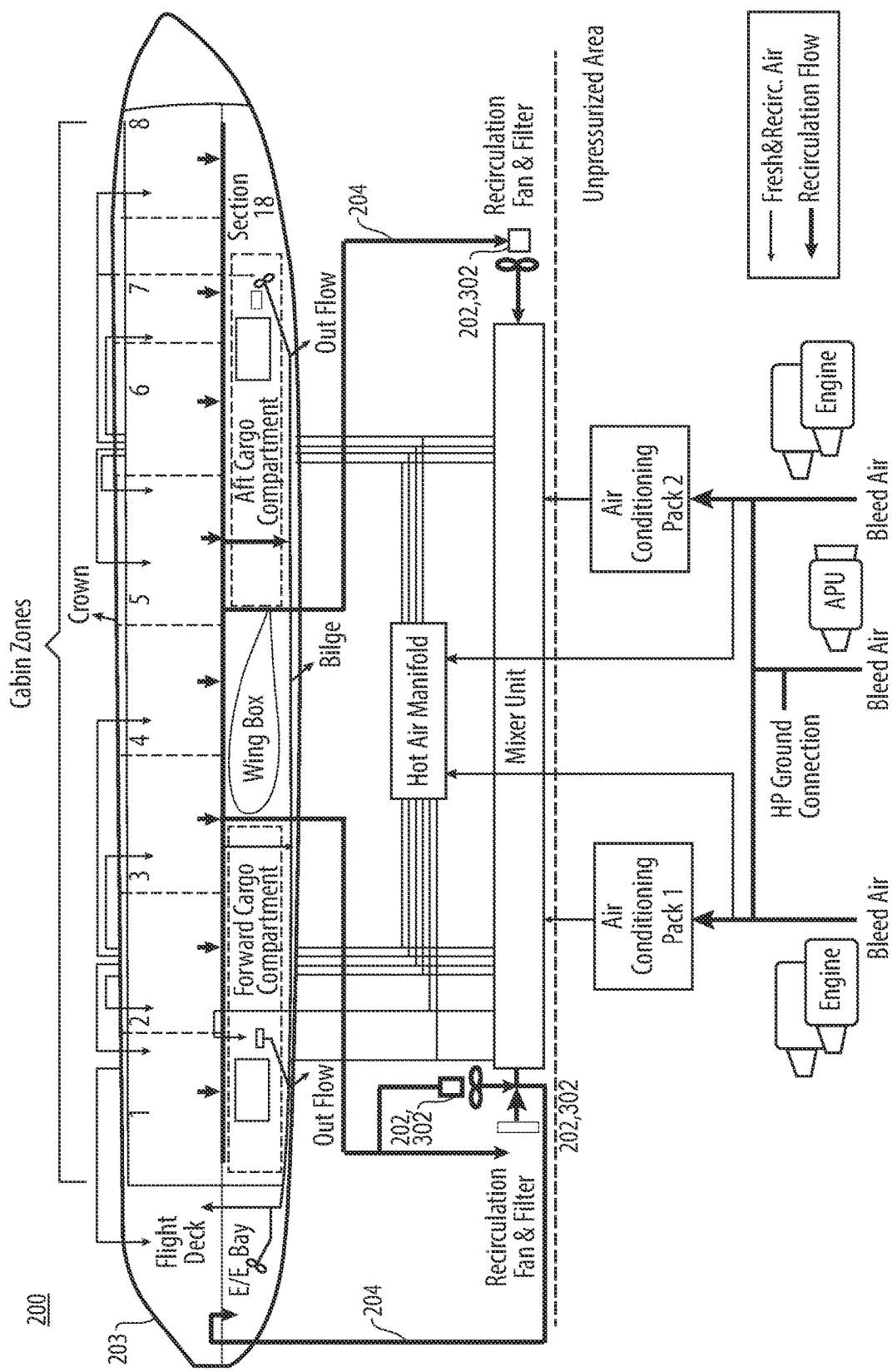
FIG. 2 is schematic of an aircraft of a showing locations where a HEPA filter according to the disclosure is located.

Reference will now be made to the drawings wherein like reference numerals identify similar structural features or aspects of the subject disclosure. For purposes of explanation and illustration, and not limitation, a schematic view of an exemplary embodiment of a method in accordance with the disclosure is shown in FIG. 1 and is designated generally by reference character 100. Other embodiments of global virus detection system, are provided in FIGS. 2 and 3, as will be described. The global virus detection system described below is used to collect a bulk sample, representative of each passenger on the aircraft and to test it to provide a bulk screening of the aircraft prior to arrival of the aircraft at a destination.

A method 100 for collecting a representative sample from an aircraft HEPA filter includes collecting a used HEPA filter after a flight 102 of a passenger aircraft, transferring the HEPA filter to a remote location 104 away from the aircraft, processing the HEPA filter 106 in order to remove an at least a portion of the collected air sample, and concentrating 108 the collected sample to be used on a pathogen identifying tester. The samples can be removed by inverted flow or by using centrifugal wash, for example. The centrifugal wash uses an sterile buffer adapted to the specific method of washing and pathogen identifying test method.

The sample can also be removed automatically or with a handheld tool. The tool includes a sponge for dragging across the HEPA filter. The sponge can then be sent off for analysis of in a tester such as PCR test, using a similar method as the one described above, where the sponge is processed through a centrifugal wash to concentrate the collected sample.

FIG. 2 shows a system 200 for collecting a representative sample from an aircraft HEPA filter. The system includes a HEPA filter 202 positioned in a recirculation flow path 204 of an aircraft 203 to collect flow path air. The HEPA filter 202 includes at least one removable strip 303 (shown in FIG. 3) attached to the HEPA filter for removing after each flight. The removable strip 303 is flexible and can attach to the HEPA filter by a loop and hook method or by using an adhesive. The removable strip is a flexible strip, and can be attached so as to not obstruct airflow through the HEPA filter. The HEPA filter 202 is accessible from inside the aircraft.

Figure 3:
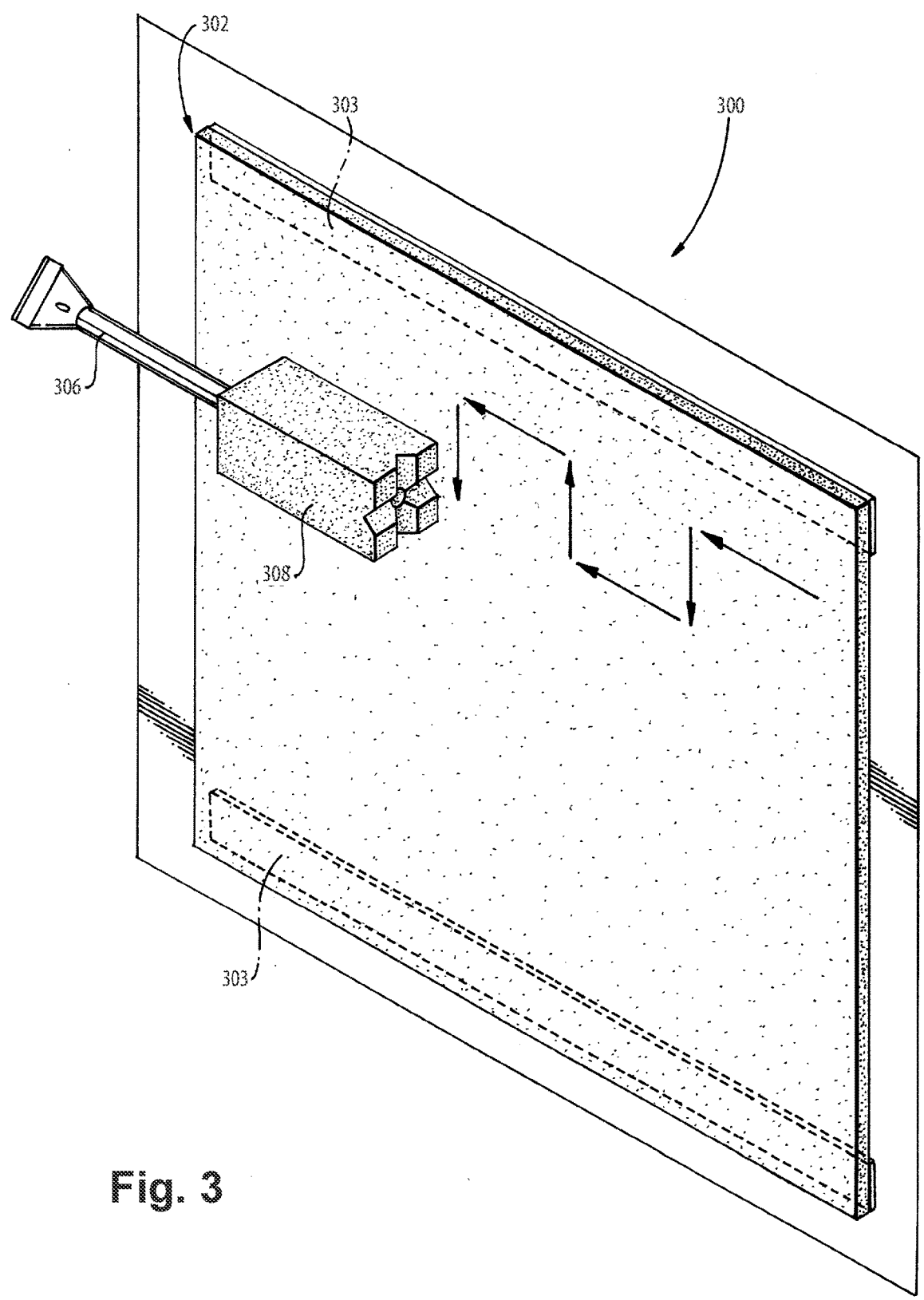
FIG. 3 is diagram of a HEPA filter and sponge according to the disclosure.

FIG. 3 shows a system 300 for collecting a representative sample from an aircraft HEPA filter 302. The system includes a HEPA filter 302 (positioned in a recirculation flow path of FIG. 2) of an aircraft to filter and collect a sample of flow path air, and a handheld wand 306 for scrubbing a portion of the HEPA filter 302 and removing a sample. The handheld wand 306 includes a sponge 308 on at least a first end thereof. The wand 306 can be moved across the body of the HEPA filter 302 in a motion involving right angles in order to properly collect a sample.

The methods and systems of the present disclosure, as described above and shown in the drawings, provide for an improved bulk data and analysis of passenger pathogens transport on an aircraft. The system provides a more efficient primary health controls at airports, adds an extra layer of health control, helps identify at early stages surging pathogens and origin, and empower their scientific research (either academic and/or commercial/institutional). While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method for collecting a representative sample from an aircraft HEPA filter comprising:
   collecting a used HEPA filter after flight;
   transferring the HEPA filter to a remote location;
   processing the HEPA filter in order to remove an air sample; and
   concentrating the collected sample to be used on a pathogen identifying test, such as a PCR tester.

2. The method of claim 1, wherein the HEPA filter is afterwards washed and made available for aircraft retrofit.

3. The method of claim 1, wherein from where the samples are removed by inverted flow.

4. The method of claim 1, wherein the samples are removed using centrifugal wash.

5. The method of claim 4, wherein the centrifugal wash uses a sterile buffer.

6. The method of claim 1, wherein the HEPA filter is configured and adapted to clean air flowing through a recirculation flow path.

7. The method of claim 1, wherein processing includes removing the sample from the HEPA filter with a handheld tool.

8. The method of claim 7, wherein the tool includes a sponge.

9. The method of claim 8, wherein the sponge is dragged across the HEPA filter in order to collect the sample.

10. The method of claim 9, wherein the sponge is processed through a pathogen identifying test.

11. The method of claim 10, wherein the sponge is processed through a centrifugal wash to concentrate the collected sample.

12. The method of claim 1, further comprising removing a portion of the HEPA filter.

13. The method of claim 12, wherein the portion is a flexible strip.

14. The method of claim 13, further comprising replacing the flexible strip with a new strip prior to the next flight.

15. A system for collecting a representative sample from an aircraft HEPA filter comprising:
   a HEPA filter positioned in a recirculation flow path of an aircraft configured to collect flow path air; and
   at least one removable strip attached to the HEPA filter for removing after each flight.

16. The system of claim 15, wherein the removable strip is flexible.

17. The system of claim 15, wherein the HEPA filter is accessible from inside the aircraft.

18. A system for collecting a representative sample from an aircraft HEPA filter comprising:
- a HEPA filter positioned in a recirculation flow path of an aircraft configured to collect flow path air; and
- a handheld wand for scrubbing a portion of the HEPA filter and removing a sample.

19. The system of claim 18, wherein the handheld wand includes a sponge on at least a first end thereof.

* * * * *